(12) United States Patent
Stettner

(10) Patent No.: US 11,116,894 B2
(45) Date of Patent: Sep. 14, 2021

(54) MEDICAL PUMP DEVICE

(71) Applicant: B. BRAUN MELSUNGEN AG, Melsungen (DE)

(72) Inventor: Jens Stettner, Melsungen (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 76 days.

(21) Appl. No.: 15/935,875

(22) Filed: Mar. 26, 2018

(65) Prior Publication Data
US 2018/0280610 A1   Oct. 4, 2018

(30) Foreign Application Priority Data

Mar. 28, 2017   (DE) ...................... 10 2017 205 251.1

(51) Int. Cl.
*A61M 5/142*   (2006.01)
*A61M 5/145*   (2006.01)
(Continued)

(52) U.S. Cl.
CPC ........ *A61M 5/14593* (2013.01); *A61M 5/152* (2013.01); *A61M 5/16854* (2013.01);
(Continued)

(58) Field of Classification Search
CPC .............. A61M 5/14593; A61M 5/152; A61M 5/16854; A61M 2205/3317;
(Continued)

(56) References Cited

U.S. PATENT DOCUMENTS 3,993,069 A    11/1976 Buckles et al.
2001/0025189 A1    9/2001 Haueter et al.
(Continued)

FOREIGN PATENT DOCUMENTS

CN    1538859 A    10/2004
CN    103874519 A    6/2014
(Continued)

OTHER PUBLICATIONS

John, Strain Gauge, Aug. 5, 2011, Instrstrumentation Today: http://www.instrumentationtoday.com/strain-gauge/2011/08/ (Year: 2011).*
(Continued)

*Primary Examiner* — Nathan R Price
*Assistant Examiner* — Tania Ismail

(57) ABSTRACT

A medical pump device for delivering a medical fluid includes a base body and elastomeric hollow membrane secured to the base body and arranged in such a way that a pump volume for filling with medical fluid is formed between the base body and hollow membrane. The hollow membrane, in an at least partially filled state of the pump volume, is elastically extended and exerts a delivery pressure on the pump volume. The medical pump device has a sensor system set up to determine the extension of the hollow membrane such that, by using the extension that is thus determined, filling level information concerning the filling state of the pump volume is determined. The medical pump device can be used in infusion or transfusion arrangements.

16 Claims, 3 Drawing Sheets

Figure 1:
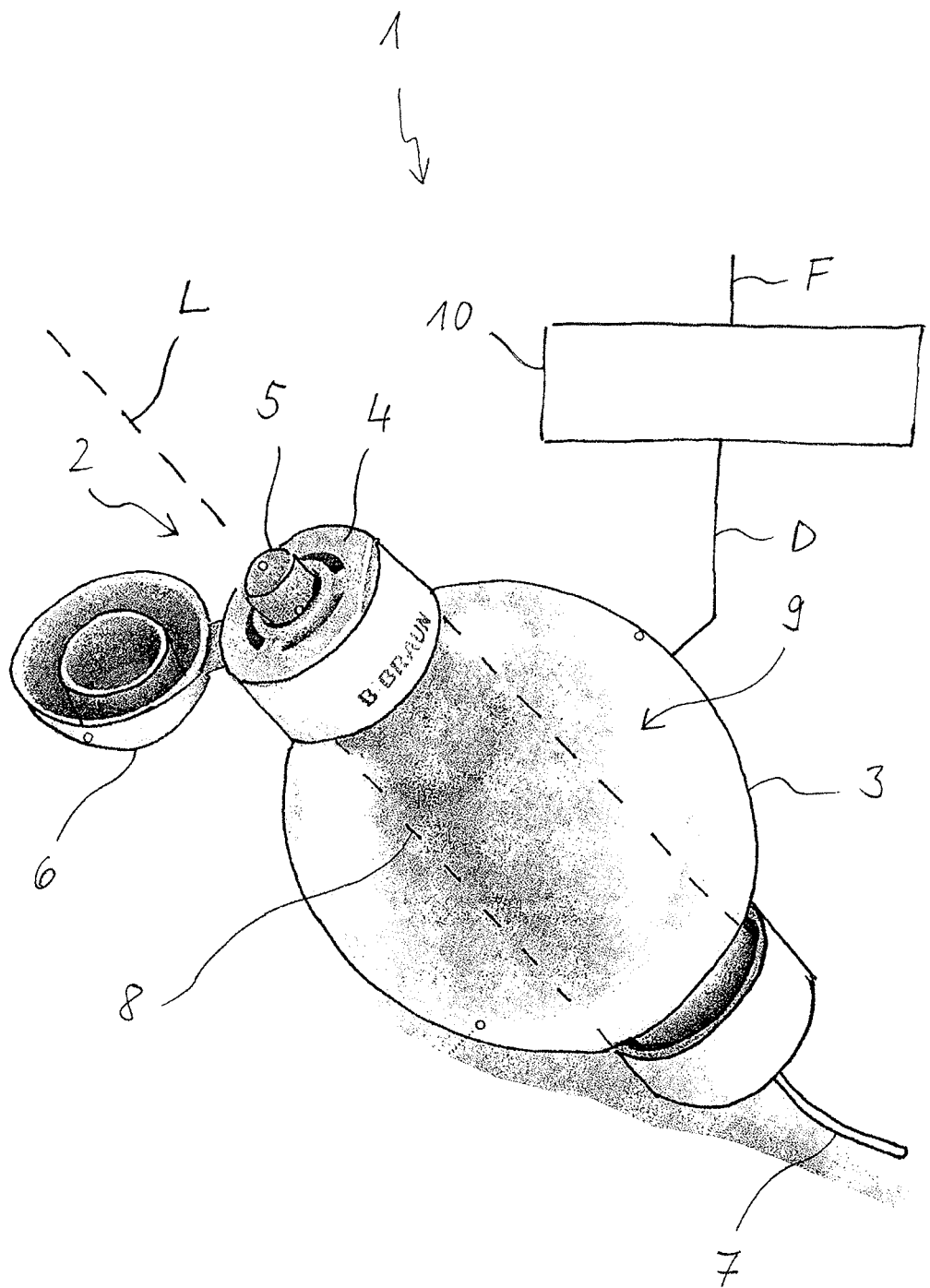

(51) Int. Cl.
 *A61M 5/168* (2006.01)
 *A61M 5/152* (2006.01)

(52) U.S. Cl.
 CPC ............... *A61M 2205/3317* (2013.01); *A61M 2205/3337* (2013.01); *A61M 2205/3382* (2013.01); *A61M 2205/3584* (2013.01); *A61M 2205/502* (2013.01); *A61M 2205/587* (2013.01)

(58) Field of Classification Search
 CPC .. A61M 2205/3337; A61M 2205/3382; A61M 2205/3584; A61M 2205/502; A61M 2205/587
 See application file for complete search history.

(56) References Cited

U.S. PATENT DOCUMENTS

| | | |
|---|---|---|
| 2003/0040722 A1 | 2/2003 | Massengale et al. |
| 2010/0033196 A1* | 2/2010 | Hayakawa ............ G06F 3/0445 324/686 |
| 2011/0009800 A1 | 1/2011 | Dam et al. |
| 2013/0053775 A1 | 2/2013 | Chiravuri et al. |
| 2013/0060211 A1 | 3/2013 | Adams |
| 2013/0274712 A1 | 10/2013 | Schecter |
| 2014/0228758 A1 | 8/2014 | Chi et al. |

FOREIGN PATENT DOCUMENTS

| | | | | |
|---|---|---|---|---|
| CN | 205796149 U | 12/2016 | | |
| DE | 19840965 A1 | 3/2000 | | |
| DE | 102013111800 A1 | 4/2015 | | |
| DE | 102016214325 A1 * | 2/2018 | ............ | A61M 5/148 |
| WO | WO-2017106408 A1 * | 6/2017 | ............ | A61M 5/152 |
| WO | WO-2018038713 A1 * | 3/2018 | .......... | A61M 5/1684 |

OTHER PUBLICATIONS

German Search Report for German Application No. 10 2017 205 251.1, dated Oct. 13, 2017, with partial translation, 9 pages.

Extended European Search Report for European Application No. 18 161 566.7, dated Aug. 21, 2018 with partial English translation, 7 pages.

Office Action received in Chinese Application No. 201810266614.2 dated May 10, 2021, with translation, 20 pages.

* cited by examiner

MEDICAL PUMP DEVICE

RELATED APPLICATION

This application claims the benefit of priority of German patent application no. DE 10 2017 205 251.1, the content of which is hereby incorporated by reference in its entirety into this application.

FIELD

The invention relates to a medical pump device for delivering a medical fluid, with a base body and with an elastomeric hollow membrane which is secured to the base body and which is arranged in such a way that a pump volume for filling with the medical fluid is formed between the base body and the hollow membrane, wherein the hollow membrane, in an at least partially filled state of the pump volume, is elastically extended and in this way exerts a delivery pressure on the pump volume.

BACKGROUND

A medical pump device of this kind is generally known in the field of medical technology and can be used to administer medical fluids in the context of outpatient infusion therapy. Such medical pump devices, which are also designated as elastomer pumps or elastomeric pump systems, have a base body and an elastomeric hollow membrane secured to the base body. The elastomeric hollow membrane has rubber-elastic extension properties and can be designed in the manner of a balloon or bladder. The hollow membrane in this way forms an outer boundary of a pump volume, which is provided to receive and discharge the medical fluid. During filling of the pump volume with the fluid, the elastomeric hollow membrane is elastically extended, wherein its surface area increases and, consequently, mechanical energy is stored in the wall of the hollow membrane. The hollow membrane elastically extended in this way exerts a delivery pressure on the pump volume. By means of this delivery pressure, the medical fluid can be delivered from the pump volume into a hose line, downstream of the pump device, and onwards into a patient-side access that is connectable to this hose line. Depending on the specification of the pump device and its use, the delivery period can be from a few minutes to several days. To be able to detect the quantity of fluid already delivered, and in some cases to be able to detect a malfunction of the pump device, it is necessary to check the filling level of the pump volume during the delivery period. For this purpose, the pump device is usually weighed by means of a balance before and during the delivery period, or the hollow membrane is measured using a tape measure. The measurement values determined in this way are documented. On the basis of these values, it is then possible to draw conclusions regarding the current filling state of the pump volume.

SUMMARY

The object of the invention is to make available a medical pump device of the type mentioned at the outset which is safer to use and easier to handle.

This object is achieved by the fact that the medical pump device has a sensor system which is set up to determine the extension of the hollow membrane such that, by using the extension that is thus determined, it is possible to determine filling level information concerning the filling state of the pump volume. By virtue of the solution according to the invention, it is possible to do without an external measuring instrument for determining the filling state. On the one hand, this permits reduction of measurement errors, since user errors when reading the external measuring instrument and errors when documenting and processing the measurement values are ruled out. On the other hand, the pump device is accordingly more user-friendly, particularly in outpatient use, since external measuring instruments of this kind do not have to be kept or carried around by the user. In this way, the solution according to the invention permits enhanced user safety and improved handling of the medical pump device. The determination of the extension of the elastomeric hollow membrane can be effected directly or indirectly. For direct detection of the extension, the sensor system can be configured to detect a change of length of at least one portion of a surface of the hollow membrane. For indirect detection of the extension, the sensor system can be configured to detect a force, a pressure, a distance or an optical measurement variable. An elastomeric hollow membrane within the meaning of the invention is to be understood as a membrane which has rubber-elastic extension properties and is designed substantially in the form of a bladder or a balloon. The material of the elastomeric hollow membrane can comprise silicone and/or rubber and/or another rubber-elastic material. Advantageously, the material of the elastomeric hollow membrane substantially comprises silicone. Advantageously, the medical pump system is configured in such a way that it is easily transportable by a user on his/her body. It is advantageous if the sensor system is arranged substantially inside a housing of the pump device, in particular substantially inside the base body. A pump device is thus obtained that is particularly compact and particularly easy to handle.

In one embodiment of the invention, the sensor system has a sensor array, which is arranged on the hollow membrane and connected thereto. The sensor array can comprise at least one sensor. The sensor can be based on a resistive, capacitive or inductive measurement principle. The connection between the sensor array and the elastomeric hollow membrane can be an adhesive connection. Advantageously, the connection between the hollow membrane and the sensor array is configured such that an extension of at least one portion of the elastomeric hollow membrane causes at least one portion of the sensor array to undergo an extension of a corresponding nature and extent. A particularly space-saving embodiment of the invention is thus achieved.

In a further embodiment of the invention, the sensor array and the hollow membrane are connected to each other by a co-extrusion method. Extrusion methods as such are generally known. In such methods, a composition to be shaped is pressed continuously, by application of pressure, through a shaping opening and in this way forms an extrudate. Accordingly, in co-extrusion methods, at least two compositions are extruded at the same time through one and the same opening and in this way form a rigidly interconnected co-extrudate. Advantageously, the sensor array and the hollow membrane are co-extruded in the form of a hose section, wherein at least one portion of the sensor array runs along the longitudinal direction of the hose and is arranged on or in a circumferential surface of the hose. Advantageously, the sensor array comprises two strips of conductive material which are arranged on or in a circumferential surface of the co-extrudate in a manner in which they are angularly offset by approximately 180 degrees to each other. Co-extrusion of this kind firstly permits particularly advantageous material properties in terms of the strength of the connection between the hollow membrane and the sensor array. Moreover, this embodiment can be produced particularly cost-effectively.

In a further embodiment of the invention, the sensor array has at least one strain gauge. The resistive measurement principle on which a strain gauge is based is generally known. It is based on the extension-dependent change of the electrical resistance of the strain gauge. In this respect, the change of the electrical resistance of the strain gauge is determined, from which conclusions are drawn concerning the change of length and thus the extension of the strain gauge and of the hollow membrane connected thereto. The filling level information can be determined ultimately from the thus determined extension of the hollow membrane. Advantageously, the strain gauge is formed at least in part by a conductive material that is co-extruded with the hollow membrane. Alternatively or additionally, the strain gauge can be formed at least in part from a conductive material that is adhesively bonded onto or into the hollow membrane. The strain gauge advantageously runs along the longitudinal direction of the hollow membrane. Alternatively or additionally, the strain gauge can run along the circumferential direction of the hollow membrane. In order to achieve a particularly high measurement sensitivity, the strain gauge can advantageously be arranged running in the circumferential direction at the location where the hollow membrane is extended radially to the greatest extent in the filled state of the pump volume.

In a further embodiment of the invention, the sensor system has an electronic evaluation unit which is configured in such a way that a measurement signal determined by means of the sensor system can be converted into a measurement value, a differential value between the measurement value and a reference value can be determined, and the filling level information can be determined using the differential value. Advantageously, the evaluation unit is connected to the sensor array and is configured to convert a voltage measurement signal into an extension measurement value. The reference value is advantageously stored in a memory unit of the evaluation unit. Advantageously, the reference value is an extension measurement value that has been determined in a substantially completely filled or emptied filling state of the pump volume. A particularly precise determination of the filling level is achieved if several reference values are stored in the form of a reference curve. Accordingly, the differential value between the measurement value and the reference value can be used to draw conclusions concerning the filling level of the pump volume and ultimately to determine filling level information. The filling level information can advantageously be determined as a relative variable in relation to the filling quantity at the start of the delivery period. Alternatively or additionally, the filling level information can be determined as a relative variable in relation to an emptied state of the pump volume. Since in this way errors are avoided in the evaluation of measurement values by a user, an embodiment of the invention is achieved that is particularly safe to use.

In a further embodiment of the invention, the sensor system has an output unit, which is configured to output the filling level information. Advantageously, the output unit can be connected to the evaluation unit. The filling level information can be output in an optical or acoustic manner or in another way that is discernible to the user. Accordingly, a person using the pump device obtains the filling level information in a particularly reliable and easily comprehensible manner.

In a further embodiment of the invention, the output unit has a display unit, which is configured to provide an optical presentation of the filling level information. The display unit can advantageously comprise a display screen. The display screen can be connected to the housing of the pump device, in particular to the base body. This embodiment of the invention permits particularly convenient detection of the filling level information by a user or by a medically trained person.

In a further embodiment of the invention, the output unit has a transmission unit, which is configured for wireless transmission of the filling level information. The filling level information can be transmitted in the form of a signal to an external display or reproduction unit, in particular a smart phone. This affords an alternative or additional way for the filling level information to be viewed by someone, for example a medically trained person, present at a location remote from the user. Accordingly, an embodiment of the invention is achieved that is particularly safe to use.

BRIEF DESCRIPTION OF THE DRAWING FIGURES

Further advantages and features of the invention will become clear from the claims and from the following description of a preferred exemplary embodiment of the invention set out in the drawings.

Figure 2:
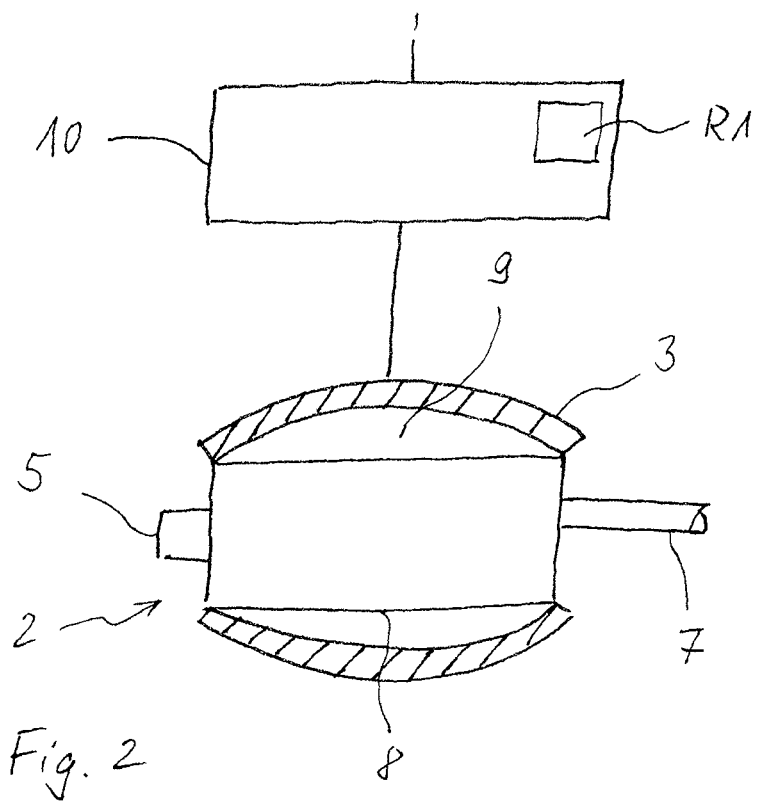
Figure 3:
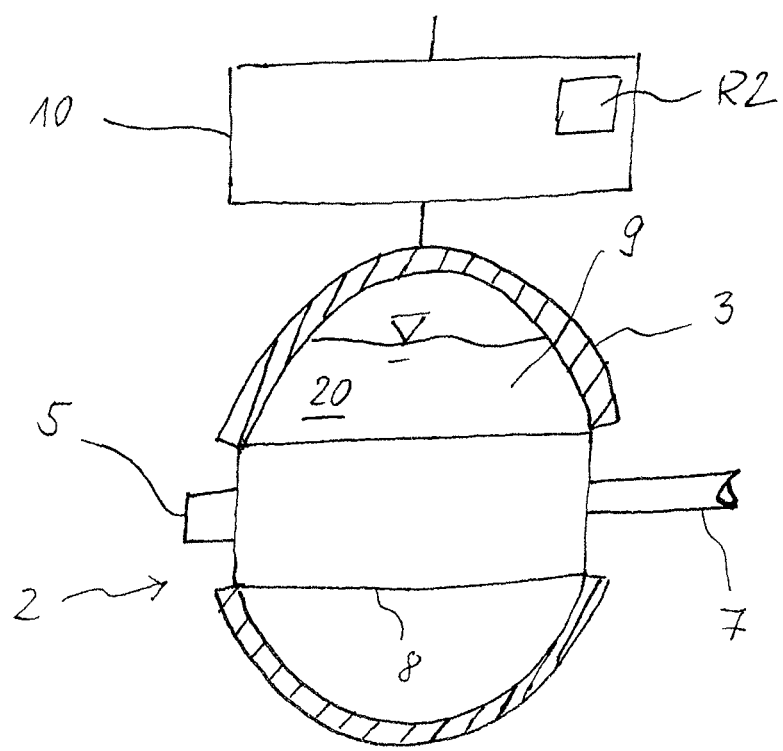
Figure 4:
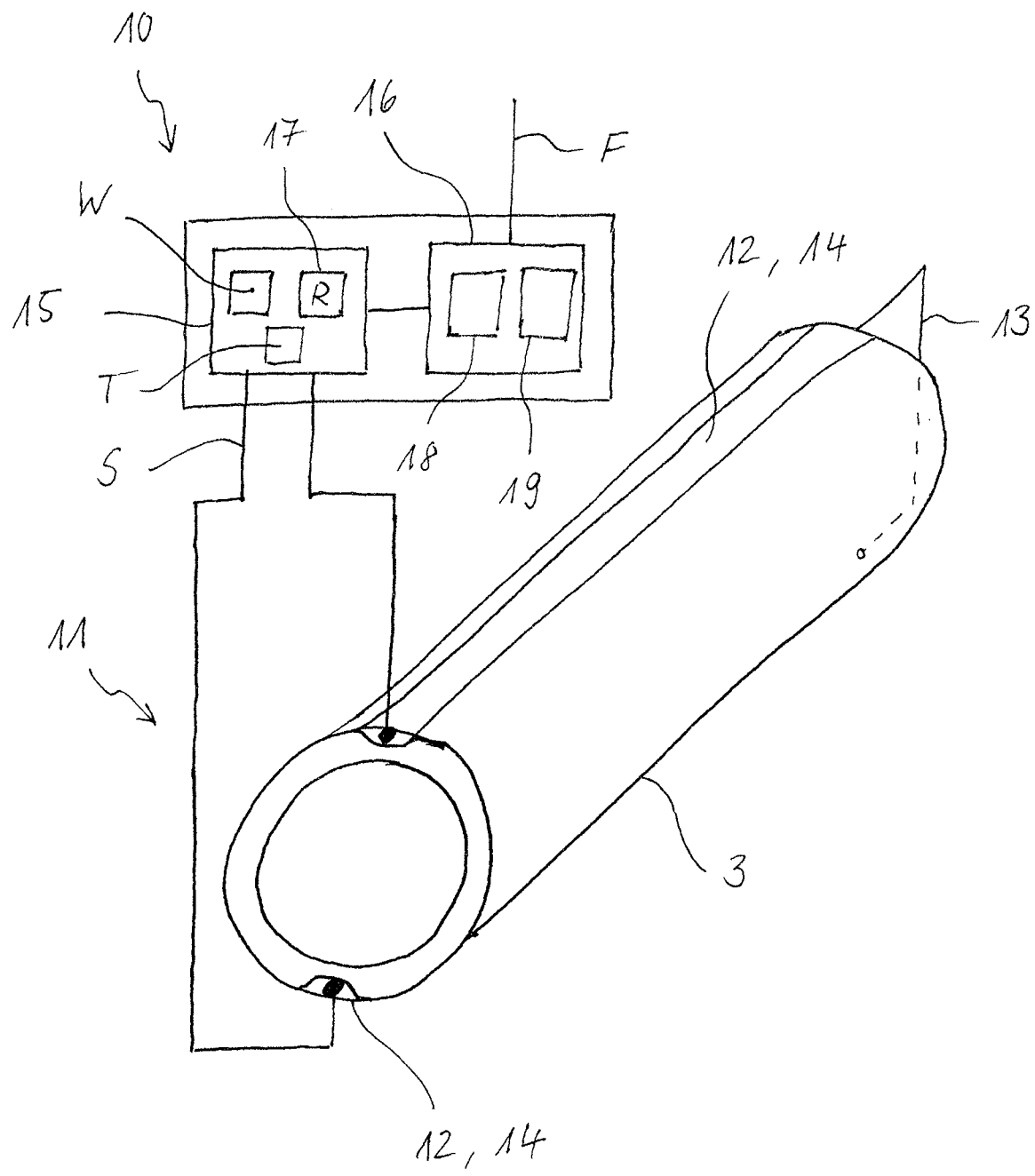

FIG. 1 shows a perspective view of a preferred embodiment of a medical pump device according to the invention with a sensor system, FIG. 2 shows a schematic view of the medical pump device from FIG. 1 in an unfilled state of the pump volume, FIG. 3 shows a schematic view of the pump device from FIG. 1 and FIG. 2 in a filled state of the pump volume, and FIG. 4 shows a schematic view of a part of the pump device from FIGS. 1 to 3 in the region of the hollow membrane and of the sensor system.

DETAILED DESCRIPTION

A medical pump device 1 according to FIGS. 1 to 4 is provided for delivering a medical fluid in the context of outpatient infusion therapy. For this purpose, the medical pump device 1 has a base body 2 and an elastomeric hollow membrane 3 secured to the base body 2. The base body 2 has a filling valve 4, a valve cap 5 and a closure cap 6, which are each arranged at the inlet side and axially with respect to the longitudinal axis L of the base body 2, although this is not mandatory. In principle, the filling valve 4 and also the valve cap 5 and the closure cap 6 can be arranged separate from the base body 2. An infusion hose 7, which is not necessarily a component part of the medical pump device 1, is arranged at the outlet side of the base body 2. In a manner not shown in any detail, the infusion hose 7 can be assigned a closure clamp, an air-separating particle filter, a flow limiter and a connector piece for attachment to a patient-side access. The elastomeric hollow membrane 3 is designed in the manner of a balloon and encloses a central part 8 (indicated in FIG. 1 by broken lines) of the base body 2 substantially coaxially with respect to the longitudinal axis L thereof. A pump volume 9 for filling with a medical fluid 20 shown schematically in FIG. 3 is formed between the central part 8 of the base body 2 and the elastomeric hollow membrane 3. In order to fill the pump volume 9 with the medical fluid 20, the closure cap 6 is brought into an opened state as shown in FIG. 1, the valve cap 5 is released, and the medical fluid 20 is introduced via the filling valve 4 into the space formed between the elastomeric hollow membrane 3 and the central part 8 of the base body 2, in other words into the pump volume 9. The elastomeric hollow membrane 3 is made of silicone elastomer and as such is rubber-elastically extensible. When the pump volume 9 is filled with the fluid 20 in this way, the surface of the elastomeric hollow membrane 3 therefore increases and consequently stores mechanical energy. The hollow membrane 3 extended rubber-elastically in this way exerts a delivery pressure on the pump volume 9. After the pump volume 9 has been filled, the valve cap 5 is closed, and the closure cap 6 is brought into a closed state. After the closure clamp assigned to the infusion hose 7 and operatively connected thereto has been opened, the medical fluid 20 can be delivered along the infusion hose 7 to the patient-side access on account of the delivery pressure exerted by means of the elastomeric hollow membrane 3.

To determine filling level information F concerning the filling state of the pump volume 9, the medical pump device additionally has a sensor system 10, which is set up to determine the extension D of the elastomeric hollow membrane 3. For the sake of clarity, the sensor system 10 is shown only schematically in FIGS. 1 to 4 and presented in its functional relationship to the other components of the pump device 1.

As can be seen from FIG. 4, the sensor system 10 has a sensor array 11 arranged on the elastomeric hollow membrane 3 and connected thereto. The elastomeric hollow membrane 3 is shown in FIG. 4 in an unassembled and therefore substantially unextended, hose-like state. The sensor array 11 has two strips 12 each connected to the outer face of the hollow membrane 3 and running in the longitudinal direction of the hollow membrane 3. The strips 12 have an electrically conductive material composition. Preferably, the strips 12 comprise a metallic material composition. Particularly preferably, the material composition has a polymer/metal or a polymer/graphite mixture or an organic semiconductor material. The strips 12 are connected to the hollow membrane 3 by a co-extrusion method and have an electrically conductive connection 13 at an end face of the hollow membrane. In this kind of sensor array 11, the electrical conductivity and therefore the electrical resistance of the strips 12 changes as the length of the hollow membrane 3 changes. The strips 12 in this way form a strain gauge 14 with which the extension D of the elastomeric hollow membrane 3 can be determined.

For this purpose, the sensor system 10 additionally has an electronic evaluation unit 15 and an output unit 16, as can be seen in detail in FIG. 4. The electronic evaluation unit 15 is connected electrically conductively to the sensor array 11, more precisely to the ends of the strips 12. In this way, a measurement signal S in the form of a voltage signal, determined by means of the sensor array 11, can be tapped at the strain gauge 14 formed by the strips 12. The evaluation unit 15 is additionally configured to convert the thus determined measurement signal S into a measurement value W and to determine a differential value T between the measurement value W and a reference measurement value R, which is stored in a memory unit 17 of the evaluation unit 15. The output unit 16 is configured to output the filling level information F and for this purpose has a display unit 18 and, alternatively or additionally, a transmission unit 19. The display unit 18 is configured to provide an optical presentation of the filling level information F and is in the form of a display screen. The transmission unit 19 is configured for wireless transmission of the filling level information F and thus permits transmission of the filling level information F to a display or reproduction unit (not shown in detail) separate from the pump device 1.

The filling level information F concerning the filling level of the pump volume 9 can be determined as follows using the medical pump device 1. In an unfilled state of the pump device 1, as shown schematically in FIG. 2, a first reference measurement value R1 in the form of an extension value of the unextended state of the hollow membrane 3 is determined by means of the sensor system 10. This reference measurement value R1 can be stored in the memory unit 17. The pump device 1 is thereafter filled with the medical fluid 20, such that the elastomeric hollow membrane 3, as can be seen in FIG. 3, is extended elastically. As a result of this elastic extension, the length of the hollow membrane 3 along the longitudinal direction L changes, wherein the strain gauge 14 likewise experiences a change of length, on account of which its electrical conductivity changes. In a thus filled state of the pump device 1, a further reference measurement value R2 is determined. This reference measurement value R2 can alternatively or additionally be stored in the memory unit 17. During emptying of the pump volume 9, the extension of the elastomeric hollow membrane 3 reduces, and hence the extension of the strain gauge 14 of the sensor array 11 reduces as well. An extension measurement value determined during such emptying can be compared, by means of the evaluation unit 15, to the reference measurement values R1, R2 stored in the memory unit 17. In this way, it is ultimately possible to determine up-to-date filling level information F concerning the filling state of the pump volume 9 during the emptying. This filling level information F can be presented visually to a user of the medical pump device 1 by means of the display unit 18 of the output unit 16. Alternatively or additionally, the filling level information F can be transmitted wirelessly to an external display or reproduction unit by means of the transmission unit 19 of the output unit 16.

The invention claimed is:

1. A medical pump device for delivering a medical fluid, the medical pump device comprising:
    a base body and an elastomeric hollow membrane which is secured to the base body and which is arranged in such a way that a pump volume for filling with the medical fluid is formed between the base body and the hollow membrane, wherein the hollow membrane, in an at least partially filled state of the pump volume, is elastically extended and exerts a delivery pressure on the pump volume; and
    a sensor system which is set up to determine an extension of the hollow membrane such that, by using the extension that is determined, filling level information concerning the filling state of the pump volume is determined;
    wherein the sensor system comprises a sensor array which is arranged on and connected to the hollow membrane; and
    wherein the sensor array is a single strain gauge comprising a first electrically conductive strip attached to an outer face of the hollow membrane and extending from a first end of the hollow membrane to the second end of the hollow membrane along a first section of the outer face, a second electrically conductive strip attached to the outer face of the hollow membrane and extending from the first end of the hollow membrane to the second end of the hollow membrane along a second section of the outer face offset from the first section of the outer face in a circumferential direction, and an electrically conductive connection extending from the first electrically conductive strip to the second electrically conductive strip at the second end of the hollow membrane, the first electrically conductive strip and the second electrically conductive strip collectively forming the single strain gauge.

2. The medical pump device according to claim 1, wherein the sensor array and the hollow membrane are connected to each other by a co-extrusion method.

3. The medical pump device according to claim 1, wherein the first electrically conductive strip and the second electrically conductive strip are coextruded with the hollow membrane.

4. The medical pump device according to claim 1, wherein the first electrically conductive strip and the second electrically conductive strip have an electrical resistance that changes as a length of the hollow membrane changes.

5. A medical pump device for delivering a medical fluid, the medical pump device comprising:
- a base body and an elastomeric hollow membrane which is secured to the base body and which is arranged in such a way that a pump volume for filling with the medical fluid is formed between the base body and the hollow membrane, wherein the hollow membrane, in an at least partially filled state of the pump volume, is elastically extended and exerts a delivery pressure on the pump volume; and
- a sensor system which is set up to determine an extension of the hollow membrane such that, by using the extension that is determined, filling level information concerning the filling state of the pump volume is determined;
- wherein the sensor system comprises a sensor array which is arranged on and connected to the hollow membrane;
- wherein the sensor array is a single strain gauge having a plurality of electrically conductive strips each attached directly to an outer face of the hollow membrane and offset from one another in a circumferential direction, and each having an electrical resistance that changes as a length of the hollow membrane changes, the plurality of electrically conductive strips collectively forming the single strain gauge, and
- wherein the single strain gauge comprises a first electrically conductive strip, a second electrically conductive strip, and an electrically conductive connection extending from the first electrically conductive strip to the second electrically conductive strip.

6. The medical pump device according to claim 1, wherein the base body comprises a filling valve arranged at an inlet side of the base body.

7. The medical pump device according to claim 6, wherein the filling valve comprises a valve cap and a closure cap separate from the valve cap.

8. The medical pump device according to claim 1, further comprising an infusion hose arranged at an outlet side of the base body.

9. The medical pump device according to claim 5, wherein the base body comprises a filling valve arranged at an inlet side of the base body.

10. The medical pump device according to claim 9, wherein the filling valve comprises a valve cap and a closure cap separate from the valve cap.

11. The medical pump device according to claim 5, further comprising an infusion hose arranged at an outlet side of the base body.

12. The medical pump device of claim 5, wherein the first and second electrically conductive strips comprise a metallic material composition.

13. The medical pump device of claim 5, wherein the first and second electrically conductive strips comprise a polymer/metal.

14. The medical pump device of claim 5, wherein the first and second electrically conductive strips comprise a polymer/graphite mixture.

15. The medical pump device of claim 5, wherein the first and second electrically conductive strips comprise an organic semiconductor material.

16. The medical pump device of claim 5, wherein the first and second electrically conductive strips are diametrically opposed to one another on the outer face of the hollow membrane.

\* \* \* \* \*